United States Patent [19]

Kagatani et al.

[11] Patent Number: 4,788,221

[45] Date of Patent: * Nov. 29, 1988

[54] PHARMACEUTICAL COMPOSITIONS COMPRISING CALCITONIN AND AN ABSORPTION-PROMOTING SUBSTANCE

[75] Inventors: Seiya Kagatani; Shunji Hasumi; Takashi Sonobe; Masayoshi Aruga, all of Shizuoka, Japan

[73] Assignee: Yamanouchi Pharmaceutical Co., Ltd., Tokyo, Japan

[*] Notice: The portion of the term of this patent subsequent to Sep. 1, 2004 has been disclaimed.

[21] Appl. No.: 46,278

[22] Filed: May 5, 1987

Related U.S. Application Data

[62] Division of Ser. No. 800,983, Nov. 22, 1985, Pat. No. 4,690,952.

[30] Foreign Application Priority Data

Nov. 26, 1984 [JP] Japan .................................. 59-248898

[51] Int. Cl.$^4$ ............................................. A61U 27/00
[52] U.S. Cl. ................................................... 514/808
[58] Field of Search ........................................ 514/808

[56] References Cited

U.S. PATENT DOCUMENTS 4,434,159 2/1984 Sekine et al. ........................ 514/12

Primary Examiner—Stanley J. Friedman
Attorney, Agent, or Firm—Burgess Ryan & Wayne

[57] ABSTRACT

Pharmaceutical compositions for intranasal administration comprising (a) calcitonin and (b) at least one absorption enhancer selected from the group consisting of benzyl alcohol, ethanol, thiamine or a salt thereof, salicylic acid or a salt thereof, capric acid or a salt thereof, Macrogol 400, pyridoxal or a salt thereof, malic acid or a salt thereof and pyrophosphoric acid or a salt thereof, in (c) a liquid diluent or carrier, suitable for application to the nasal mucosa.

6 Claims, No Drawings

PHARMACEUTICAL COMPOSITIONS COMPRISING CALCITONIN AND AN ABSORPTION-PROMOTING SUBSTANCE

This is a division of application Ser. No. 800,983 filed Nov. 22, 1985 now U.S. Pat. No. 4,690,952.

BACKGROUND OF THE INVENTION

1. Field of the Invention

The present invention relates to a intranasal (via nasal route) pharmaceutical composition comprising calcitonin as an active ingredient and more particularly, to an excellent calcitonin intranasal composition containing a specific absorption enchancer.

2. Description of the Related Art

Calcitonin is a polypeptide hormone having various pharmaceutical activities which is used for treatment of osteoporosis, hypercalcemia, Paget's disease, etc.

Calcitonin is decomposed in the gastrointestinal tract by digestive juice, like ordinary pharmacologically active peptides so that oral administration of calcitonin is not available therapeutically. In addition, due to poor absorption, calcitonin is generally administered by injection. However, injections are extremely painful and this route of administration is not used. Thus inconvenience and a cost problem encountered.

Recently, it has been found that by application of calcitonins via intranasal route, effects simmilar to conventional intramuscular injection are exhibited and, various compositions of intranasal calcitonin composition have been proposed. However, a polypeptide having a large molecular weight such as calcitonin is absorbed intranasally only with difficulty. Therefore, as absorption enhancers, for example, surface active agents are generally incorporated (Published Unexamined Japanese patent application Nos. 89619/84 and 130820/84). In this case, both amphoteric and cationic surface active agents are employed; it is said, however, that nonionic type surface active agents, inter alia, polyoxyethylene lauryl ether, are particularly excellent in absorption acceleration properties. However, this polyether type surface active agent exhibits the undesirable property of destroying the nasal membrane. Thus, the surface active agent has a strong toxicity to tissue and is therefore undesirable for use as it is.

DETAILED DESCRIPTION OF THE INVENTION

As a result of extensive investigations of dosage forms for intranasal administration capable of enhancing absorption of calcitonin and providing for practical use, the present inventors have found that excellent results can be achieved by incorporating a certain absorption enhancer into the calcitonin-containing intranasal medical composition and have reached the present invention. The present invention relates to a intranasal medical composition calcitonin and (b) at least one absorption enhancer selected from the group consisting of benzyl alcohol, ethanol, thiamine or a salt thereof, salicylic acid or a salt thereof, capric acid or a salt thereof, Macrogol 400*, pyridoxal or a salt thereof, malic acid or a salt thereof and pyrophosphoric acid or a salt thereof, which are contained in a liquid dilution or a carrier suitable for applying to nasal membrane.

*polyethylene glycol 400

As calcitonins used in the present invention, various kinds of calcitonins such as salmon calcitonin, human calcitonin, salcatonin, porcine calcitonin, etc. can be used.

The substance that enhances absorption of calcitonins is selected from benzyl alcohol, ethanol, thiamine, salicylic acid, capric acid, Macrogol 400*, pyridoxal, malic acid and pyrophosphoric acid. Among these absorption enhancers, compounds capable of forming salts may be used in the form of the salts thereof. In the case of basic compounds such as pyridoxal, thiamine, etc., the hydrochloride, the nitrate, etc. are employed. In the case of acidic substances such as pyrophosphoric acid, salicylic acid, malic acid, capric acid, etc., the sodium salts, potassium salts, etc. are employed.

The absorption enhancer may be used singly or in combination of two or more other enhancers.

The pernasal medical composition of the present invention may be in the form of an aqueous solution, hydrogel or solid powders.

The aqueous solution is prepared by dissolving calcitonins and the absorption enhancer in water or a buffer solution in a conventional manner. In this case, additives are added to and dissolved in the aqueous solution, if necessary. It is preferred that pH of the aqueous solution is between 3 and 5 in view of stability.

As the buffer, citrates, tartarates, malates, etc. are employed, in a preferred pH range of 3 to 5.

As the additives, sterilizers, preservatives, tackifiers, surface active agents, stabilizers, etc. conventionally used for pernasal agents can be incorporated.

As the sterilizer and the preservative, conventional ones may be used and examples include p-oxybenzoates, propylene glycol, benzetonium chloride, sorbic acid (Na), etc.

As the tackifier, polyvinyl alcohol, polyvinyl pyrrolidone, dextran, etc. may be employed.

The surface active agent is added as a dispersing and emulsifying agent for various additives; nonionic surface active agents that have little irritation to the membrane are preferred. As these nonionic surface active agents, for example, polyoxyethylene monostearate, polyoxyethylene sorbitan monooleate, polyoxyethylene-hydrogenated castor oil, etc. are used.

As the stabilizer, mention may be made of gelatin or albumin.

As the mode of administration, there may be used a method for dropwise addition or spraying using a dropping container, a sprayer or a nasal aerosol applicator for administration.

In the case of a powdery form, mannitol, inositol, glucose, etc. are additionally added in a manner similar to the case of ordinary powders; after dissolving and then freeze-drying, the resulting solid is pulverized into fine powders, which are administered by a intranasal route. Such powders are administered in such a manner that they are packed in a capsule, the capsule is set in a spraying device and a needle is penetrated through the capsule to make pores at the top and the bottom of the capsule and air is sent via rubber balls, etc. to blow the powders out; etc. In case that volatile liquid components such as ethanol, benzyl alchol, etc. are used as the absorption promoters, the powdery shape is not suitable.

In the case of an aqueous gel, calcitonin is formed into an aqueous gel using gel bases conventionally used, for example, natural gums, methyl celluloses, acrylic polymers, vinyl polymers or polysaccharides, etc.

The proportions of calcitonin as an active ingredients, the absorption enhancer and various additives to be used in the medical composition of the present invention are not particularly limited but appropriately determined depending upon dosage form of a solution, a gel or powders, etc. In case that the composition of calcitonins for pernasal drops is in the form of an aqueous solution, calcitonin is formulated in a concentration of generally from 200 to 6000 IU/ml, preferably 500 to 2000 IU/ml; the dose is preferably 0.05 to 0.2 ml/time and the number of administration is preferably 1 to 5 times daily. The amount of incorporated absorption enhancer various but in the case of an aqueous solution, it is appropriate tha the absorption enhancer be used in a range of 0.05 to 15% (w/v); a particularly preferred range is 1.0 to 10% (w/v) with respect to ethanol and 0.1 to 5% (w/v) with respect to the other absorption enhancers.

By the use of a specific absorption enhancer in the calcitonin intranasal composition of this invention, efficiency of absorbing across the membrane of the nasal cavity is enhanced and it can be said that the calcitonin intranasal composition is excellent.

Examples and Effects

Hereafter the present invention will be described in more detail with reference to the examples but is not deemed to be limited thereto.

Preparation Example 1

| | per 1 ml |
|---|---|
| Salmon calcitonin | 350 IU |
| Citric acid hydrate | 12.2 mg |
| Sodium citrate | 12.4 mg |
| Absorption enhancer | (cf. Table 1) |

TABLE 1

| | Absorption enhancer | Amount (mg) |
|---|---|---|
| a | Control | — |
| b | Benzyl alcohol | 1.0 |
| c | Benzyl alcohol | 10 |
| d | Ethanol | 50 |
| e | Malic acid | 30 |
| f | Sodium caprate | 10 |
| g | Sodium salicylate | 10 |
| h | Macrogol 400 | 10 |
| i | Thiamine hydrochloride | 10 |
| j | Pyridoxal hydrochloride | 10 |
| k | Sodium pyrophosphate | 30 |
| l | Sodium pyrophosphate | 30 |
|   | Thiamine hydrochloride | 30 |
| m | Sodium pyrophosphate | 30 |
|   | Benzyl alcohol | 10 |

Salmon calcitonin and the absorption enhancer were dissolved in a solution of citric acid monohydrate and sodium citrate in a concentration twice that shown in the table, respectively. After pH was adjusted to 4.0 using a 1N aqueous hydrochloric acid solution or a 1N aqueous sodium hydroxide solution, water is added to make 1 ml. Both are mixed in equal volumes. The salicylic acid preparation was a suspension. The sodium caprate preparation was adjusted to a pH of 8.

Example 1

Sprague Dawley strain male rats (115–145 g) fasted for 18 hours were anesthesized with pentobarbital (50 mg/kg, intraperitoneal injection). Aqueous calcitonin preparations a through m prepared in Preparation Example 1 were administered to the rats in a dose of 5 IU/kg.

Administration was performed by using a microsyringe (2 $\mu$l) having connected a polyethylene tube (PE 10, Clay Adams) therewith and injecting about 2 $\mu$l at a distance of 5 to 6 mm from the nasal septum depending upon the body weight. Evaluation of absorption of the calcitonin preparation through the nasal membrane was performed by measuring the concentration of calcium in serum. The calcium concentration was quantitatively determined using a calcium meter (CA-30, Joko). The rats were sacrificed prior to administration and 1, 2 and 3 hours after administration. Blood was collected from the descending large vein. The results are shown in Table 2. The data shown in Table 2 are mean values of 3 or more rats.

TABLE 2

Concentration of Calcium in Serum after intranasal Administration of Calcitonin (5 IU/kg)

| | Absorption Enhancer | Concentration % | Ca mg % Hours after | | |
|---|---|---|---|---|---|
| | | | 1 | 2 | 3 hours |
| a | Control | — | 10.65 | 10.24 | 10.81 |
| b | Benzyl alcohol | 0.1 | 9.01 | — | 11.17 |
| c | Benzyl alcohol | 1 | 8.41 | 10.53 | 10.73 |
| d | Ethanol | 5 | 8.46 | 11.12 | 11.14 |
| e | Malic acid | 3 | 8.87 | 11.59 | 10.24 |
| f | Sodium caprate | 1 | 8.67 | — | — |
| g | Sodium salicylate | 1 | 8.56 | 9.33 | 10.71 |
| h | Macrogol 400 | 1 | 8.71 | 11.24 | 11.18 |
| i | Thiamine hydrochloride | 1 | 8.48 | 9.59 | 11.37 |
| j | Pyridoxal hydrochloride | 1 | 8.85 | — | 11.70 |
| k | Sodium pyrophosphate | 3 | 8.97 | 9.21 | 9.84 |
| l | Sodium pyrophosphate Thiamine hydrochloride | 3 3 | — | 8.68 | — |
| m | Sodium pyrophosphate Benzyl alcohol | 3 1 | — | 8.64 | — |

Calcium concentration in serum prior to administration: 10.67 mg%

From Table 2, it is noted that Ca concentration in serum is significantly reduced by the addition of a specific absorption enhancer as compared to the control.

In a manner similar to Preparation Example 1, calcitonin intranasal compositions shown in the following preparation examples were prepared. These calcitonin solutions provide reduction of the calcium concentration in serum as in Example 1.

Preparation Example 2

| Porcine calcitonin | 1400 IU |
|---|---|
| Benzyl alcohol | 10 mg |
| Malic acid | 13.4 mg |
| Methyl p-oxybenzoate | 5 mg |
| Propyl p-oxybenzoate | 2 mg |

A 1N aqueous sodium hydroxide solution was added to adjust pH to 4.0. Water was added to make the final volume 1 ml.

Preparation Example 3

| Elcatonin | 1400 IU |
|---|---|
| Salicylic acid | 10 mg |
| Benzetonium chloride | 0.1 mg |

-continued

| | |
|---|---|
| Tartaric acid | 30 mg |
| Hydroxypropyl cellulose | 20 mg |

A 1N aqueous sodium hydroxide solution was added to adjust pH to 4.0. Water was added to make the final volume 1 ml.

Preparation Example 4

| | |
|---|---|
| Salmon calcitonin | 1400 IU |
| Macrogol 400 | 10 mg |
| Thiamine hydrochloride | 10 mg |
| Citric acid monohydrate | 12.2 mg |
| Sodium citrate | 12.4 mg |

Water was added to make the final volume 1 ml.

Preparation Example 5

| | |
|---|---|
| Salmon calcitonin | 14000 IU |
| Sodium pyrophosphate | 300 mg |
| Benzyl alcohol | 100 mg |
| Benzetonium chloride | 1 mg |
| Citric acid monohydrate | 122 mg |
| Sodium citrate | 124 mg |

5N hydrochloric acid was added to adjust pH to 4.0. Water was added to make the final volume 10 ml.

Preparation Example 6

| | |
|---|---|
| Salmon calcitonin | 14000 IU |
| Sodium pyrophosphate | 300 mg |
| D-Ribose | 300 mg |
| Benzetonium chloride | 1 mg |
| Citric acid monohydrate | 122 mg |
| Sodium citrate | 124 mg |

5N Hydrochloric acid was added to adjust pH to 4.0. Water was added to make the final volume 10 ml.

What is claimed is:

1. An intranasal pharmaceutical composition of calcitonin suitable for applying to nasal mucous membrane, said composition comprised of (a) from about 200 to 6000 IU/ml of calcitonin, (b) from about 0.05 to about 15 weight percent by volume of an absorption enhancer consisting of salicylic acid or a salt thereof, and (c) a pharmaceutically acceptable carrier.

2. An intranasal pharmaceutical composition of calcitonin according to claim 1 wherein said absorption enhancer is sodium salicylate.

3. An intranasal pharmaceutical composition of calcitonin according to claim 1 wherein said absorption enhancer is potassium salicylate.

4. A method of administering a calcitonin to a subject requiring calcitonin treatment, which method comprises administering to said subject requiring such treatment, from about 200 to 600 IU/ml of a composition as defined in claim 1 via the nasal route.

5. An intranasal pharmaceutical composition of calcitonin according to claim 1 wherein said absorption enhancer is salicylic acid.

6. An intranasal pharmaceutical composition of calcitonin according to claim 1 wherein said absorption enhancer is a salt of salicylic acid.

* * * * *